(12) United States Patent
Oakes

(10) Patent No.: US 10,682,461 B2
(45) Date of Patent: Jun. 16, 2020

(54) PUMPING CHAMBER WITH RIB

(71) Applicant: ViCentra B.V., Utrecht (NL)

(72) Inventor: Timothy William Oakes, Swansea (GB)

(73) Assignee: VICENTRA B. V., Utrecht (NL)

( * ) Notice: Subject to any disclaimer, the term of this patent is extended or adjusted under 35 U.S.C. 154(b) by 28 days.

(21) Appl. No.: 15/771,693

(22) PCT Filed: Dec. 12, 2016

(86) PCT No.: PCT/EP2016/080686
§ 371 (c)(1),
(2) Date: Apr. 27, 2018

(87) PCT Pub. No.: WO2017/118537
PCT Pub. Date: Jul. 13, 2017

(65) Prior Publication Data

US 2018/0344925 A1 Dec. 6, 2018

(30) Foreign Application Priority Data

Jan. 6, 2016 (GB) .................................. 1600231.3

(51) Int. Cl.
*A61M 5/142* (2006.01)
*F04B 43/02* (2006.01)
(52) U.S. Cl.
CPC .... *A61M 5/14224* (2013.01); *A61M 5/14244* (2013.01); *F04B 43/02* (2013.01)
(58) Field of Classification Search
CPC ..... A61M 5/14224; F15B 15/10; F04B 43/02; F04B 45/04
See application file for complete search history.

(56) References Cited

U.S. PATENT DOCUMENTS

| 4,395,259 | A | 7/1983 | Prestele et al. | |
|---|---|---|---|---|
| 6,709,417 | B1* | 3/2004 | Houle | A61M 5/14224 604/153 |
| 8,425,493 | B2* | 4/2013 | Lord | A61M 5/14224 604/131 |
| 2004/0126254 | A1 | 7/2004 | Chen et al. | |
| 2004/0204673 | A1* | 10/2004 | Flaherty | A61M 5/14248 604/65 |
| 2009/0092503 | A1 | 4/2009 | Meng et al. | |
| 2011/0066108 | A1 | 3/2011 | Geipel et al. | |

FOREIGN PATENT DOCUMENTS

| CH | 702418 A1 | 6/2011 |
|---|---|---|
| WO | WO 02/068015 A2 | 9/2002 |
| WO | WO 03/099351 A2 | 12/2003 |

OTHER PUBLICATIONS

Jun. 30, 2016 UKIPO Search Report for GB 16 00231.3.
Mar. 8, 2017 ISR for PCT/EP2016/080686.
Mar. 8, 2017 Written Opinion of Int'l Searching Authority PCT/EP2016/080686.

* cited by examiner

*Primary Examiner* — Michael Leslie
(74) *Attorney, Agent, or Firm* — Hahn Loeser & Parks LLP

(57) ABSTRACT

A pumping chamber (8) for a micro-pump (2), the pumping chamber having a volume of 100 micro litres or less bounded by an interior wall and having an inlet (87) and an outlet (88), wherein the interior wall has at least one inwardly projecting rib (70) having a first end adjacent the inlet and a second end adjacent the outlet.

20 Claims, 8 Drawing Sheets section A-A section B-B section C-C

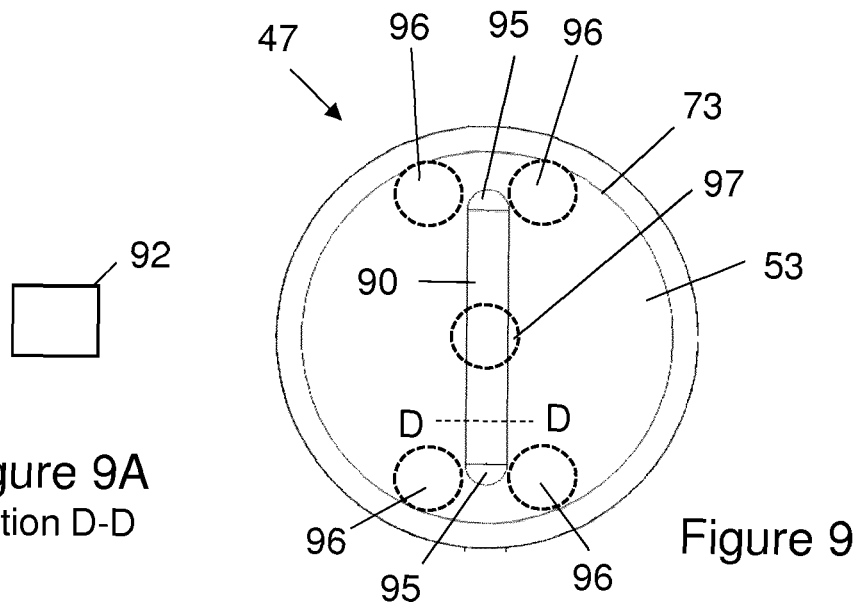
Figure 9A
section D-D
Figure 9
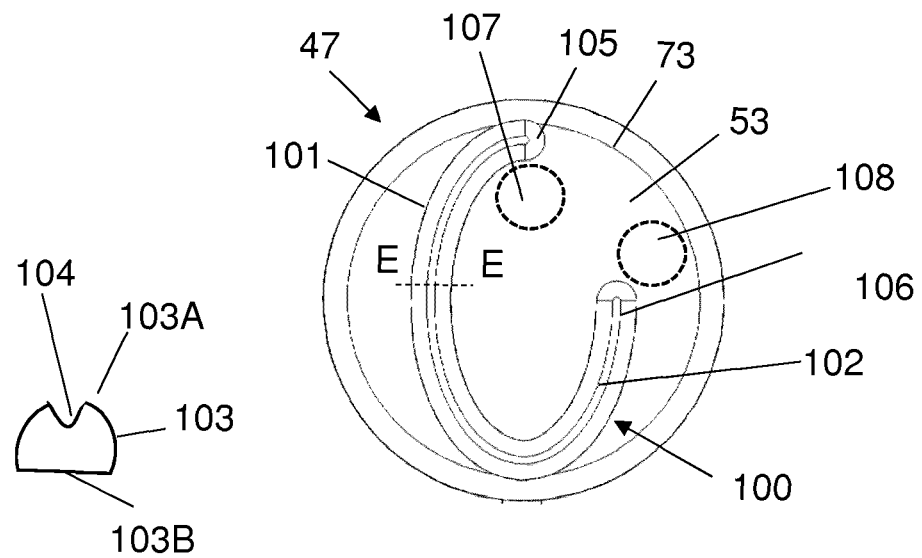
Figure 10A
section E-E
Figure 10

PUMPING CHAMBER WITH RIB

The present application is a § 371 submission of international application no. PCT/EP2016/080686, filed 12 Dec. 2016 and published in the English language on 13 Jul. 2017 with publication no. WO 2017/118537 A1, which claims the benefit of the filing date of GB 16 00231.3 filed 6 Jan. 2016.

FIELD OF THE INVENTION

The present invention relates to a pumping chamber for a micro-pump, and to an infusion system for the infusion of a liquid therapeutic product.

BACKGROUND OF THE INVENTION

Infusion systems for the infusion of liquid therapeutic products into the human or animal body are known in the art, e.g. from U.S. Pat. No. 4,395,259. Such systems are particularly, though not exclusively, intended for the infusion of insulin into the body for diabetes therapy. The system has an infusion device which may be implanted or worn externally on the body, and a remote controller that can wirelessly monitor the function of the infusion device. The infusion device includes a pump (typically a micro-pump) connected to an infusion set, a reservoir of the therapeutic product, control electronics and a battery power supply. The infusion set includes a cannula attached subcutaneously to the patient's skin.

When the infusion device is first assembled, air is likely to be present within the various cavities of the device. The air is required to be evacuated during the first filling and priming of the device ready for use, since any air remaining will form air bubbles within the pumping chamber, which may otherwise lead to under dosing.

SUMMARY OF THE INVENTION

A first aspect of the invention provides a pumping chamber for a micro-pump, the pumping chamber having a volume of 100 microlitres or less bounded by an interior wall and having an inlet and an outlet, wherein the interior wall has at least one inwardly projecting rib having a first end adjacent the inlet and a second end adjacent the outlet.

A further aspect of the invention provides an infusion system for the infusion of a liquid therapeutic product, comprising a reservoir for storing the liquid therapeutic product, and a pump having the pumping chamber according to the first aspect.

When the pumping chamber is primed, the fluid filling the pumping chamber should form a single fluid front to avoid air bubbles forming within the pumping chamber volume. Various forces act on the fluid as the pumping chamber is primed, including fluid surface tension, gravity, and fluid dynamic forces resulting from e.g. the flow rate and pressure of the fluid entering the pumping chamber via the inlet. Depending on the pumping chamber volume and the fluid dynamics the fluid surface tension may be the dominant force acting on the fluid in the pumping chamber during priming, or gravity may be the dominant force. Priming the pumping chamber may be user controlled and so there will likely be variations in the fluid dynamic forces during priming as a user may fill the pumping chamber either rapidly or more slowly.

The inwardly projecting rib has been found to promote the formation of a single fluid front during priming of the pumping chamber. In particular the rib has a first end adjacent the inlet and a second end adjacent the outlet. This has been found to draw fluid along the rib from adjacent the outlet towards the inlet during priming, thereby promoting the formation of a single fluid front and avoiding the formation of trapped air bubbles within the pumping chamber. The filling of the pumping chamber may therefore be either with or against the action of gravity. The rib preferably occupies only a small fraction of the volume of the pumping chamber.

The inwardly projecting rib may have a variety of different cross sections. For example, the rib may have a generally wedge shaped cross section. The rib may have a base connected to the interior wall and be tapered to an apex opposite the base of the rib, or the rib may have an edge projecting generally perpendicular to the base of the rib. Alternatively, the inwardly projecting rib may have a generally dome shaped cross section, e.g. the rib may have a base connected to the interior wall and a domed peak opposite the base. The domed peak may include a channel recess. Alternatively, the rib may have a rectangular shaped cross section, e.g. a square section.

The inwardly projecting rib may have a height and a length, and the rib height may reduce in the length direction towards at least one of the first and second ends of the rib.

The at least one inwardly projecting rib may be formed as a plurality of ribs, or as a plurality of rib portions. The plurality of ribs or rib portions may intersect.

The inwardly projecting rib may include a substantially straight portion and/or a curved portion. The rib having a curved portion may form an open or incomplete loop.

A portion of the interior wall may be movable so as to vary the pumping chamber volume. The movable portion of the wall may be movable relative to the inlet and the outlet. The inwardly projecting rib may be connected to and movable with the movable portion of the interior wall.

The movable portion of the wall may be formed of resilient elastomeric material. Alternatively the movable portion of the wall may be a rigid component. The rigid movable portion of the wall may be sealed.

The pumping chamber may be configured such that fluid flow through the inlet is substantially perpendicular to a portion of the interior wall having the inwardly projecting rib.

The pumping chamber may include only a single inlet and a single outlet, or may include multiple inlets and/or outlets. Each inlet and outlet may comprise a one-way valve, e.g. a passive normally closed one-way check valve.

The infusion system may be adapted for the infusion of one of a variety of liquid therapeutic products. In one application the infusion system is an insulin infusion system for continuous subcutaneous insulin infusion therapy.

The pumping chamber and the reservoir may be provided in a cartridge. The cartridge may be disposable and removably attached to a durable housing part of the infusion system.

BRIEF DESCRIPTION OF THE DRAWINGS

Embodiments of the invention will now be described with reference to the accompanying drawings, in which:

FIG. 9 illustrates a second alternative embodiment of the inwardly projecting rib;

FIG. 9A shows a cross section through the rib portion of FIG. 9 at D-D.

FIG. 10 illustrates a third alternative embodiment of the inwardly projecting rib; and FIG. 10A shows a cross section through the rib portion of FIG. 9 at E-E.

DETAILED DESCRIPTION OF EMBODIMENT(S)

Figure 1:
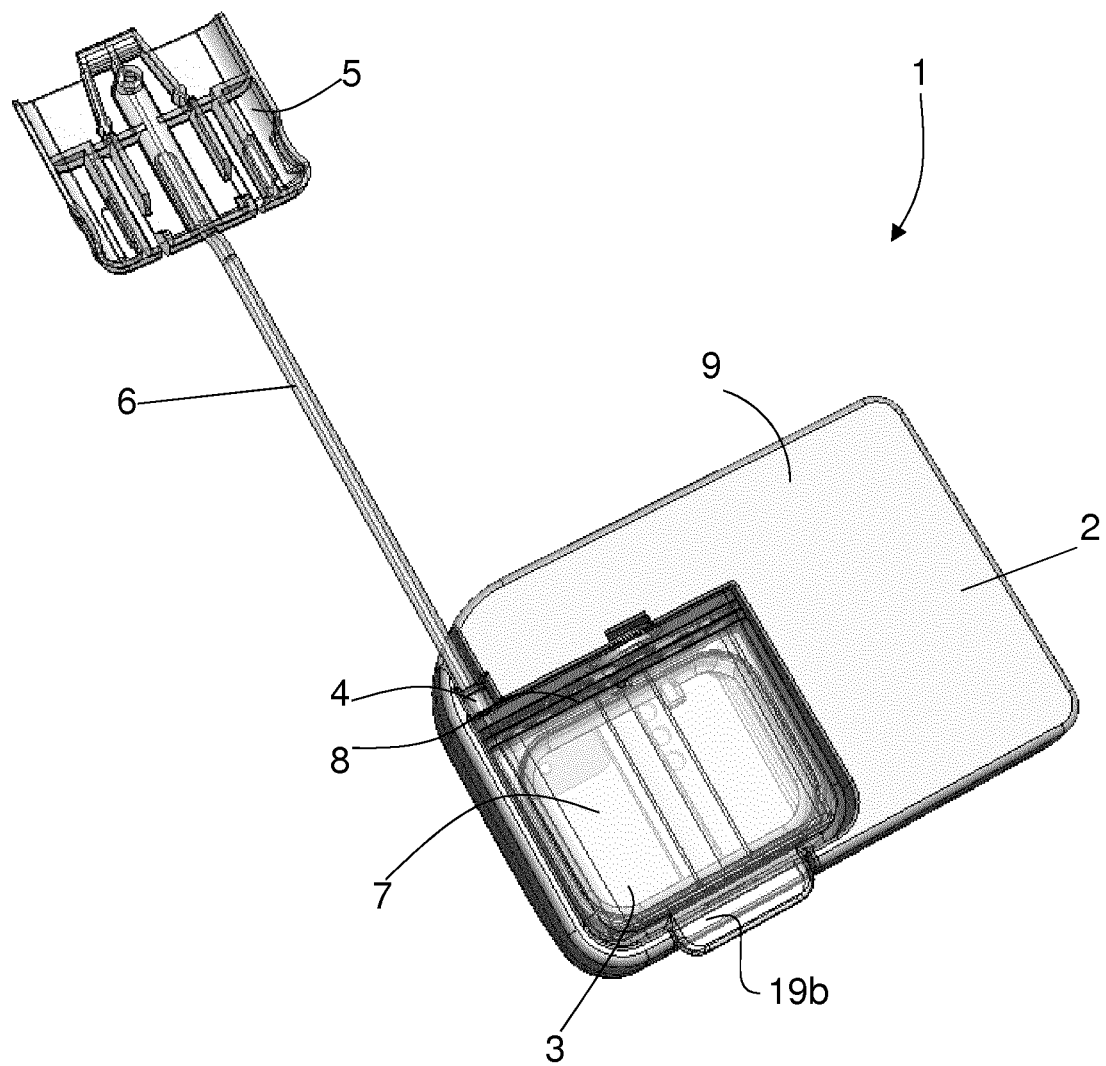
FIG. 1 illustrates a wearable part of an external infusion system.

FIG. 1 shows the wearable part of an external infusion system 1 for the continuous subcutaneous infusion of insulin into the human body through repetitive small pulses of infusion. The infusion system 1 comprises a pump part 2, a cartridge 3 having an outlet port 4 connected to an infusion set 5 via an infusion tube 6.

The infusion set 5 includes a subcutaneous cannula and an adhesive mount for adhering the infusion set to the patient's skin. The cannula is typically made of flexible plastic so as not to cause discomfort for the patient during use. The infusion set is typically installed into a spring loaded insertion device together with a steel needle surrounding the cannula. Upon insertion, the steel needle is removed leaving the cannula in place. Alternative infusion sets, which may replace the infusion set shown in FIG. 1, comprise a steel needle instead of the cannula.

Depending on the desired positioning of the pump part 2 with respect to the infusion set 5 during use the length of the infusion tube 6 may be longer or shorter than that shown in FIG. 1, and indeed the infusion set 5 may be coupled directly to the output port 4 of the pump where close coupling of the infusion set 5 and the pump part 2 is desired, thereby avoiding the need for the flexible infusion tube 6.

The cartridge 3 includes a reservoir 7 for storing a supply of insulin and a pumping chamber 8. The pump part 2 contains an actuator, a rechargeable battery power supply and control electronics for controlling the actuator.

The cartridge 3 is removably attachable to a housing 9 of the pump part 2 such that when the cartridge 3 is attached to the housing 9 a drive member of the actuator is operatively coupled to the pumping chamber 8 for delivering a supply of insulin from the reservoir 7 to the outlet port 4 and into the infusion set 5 via the infusion tube 6.

Figure 2:
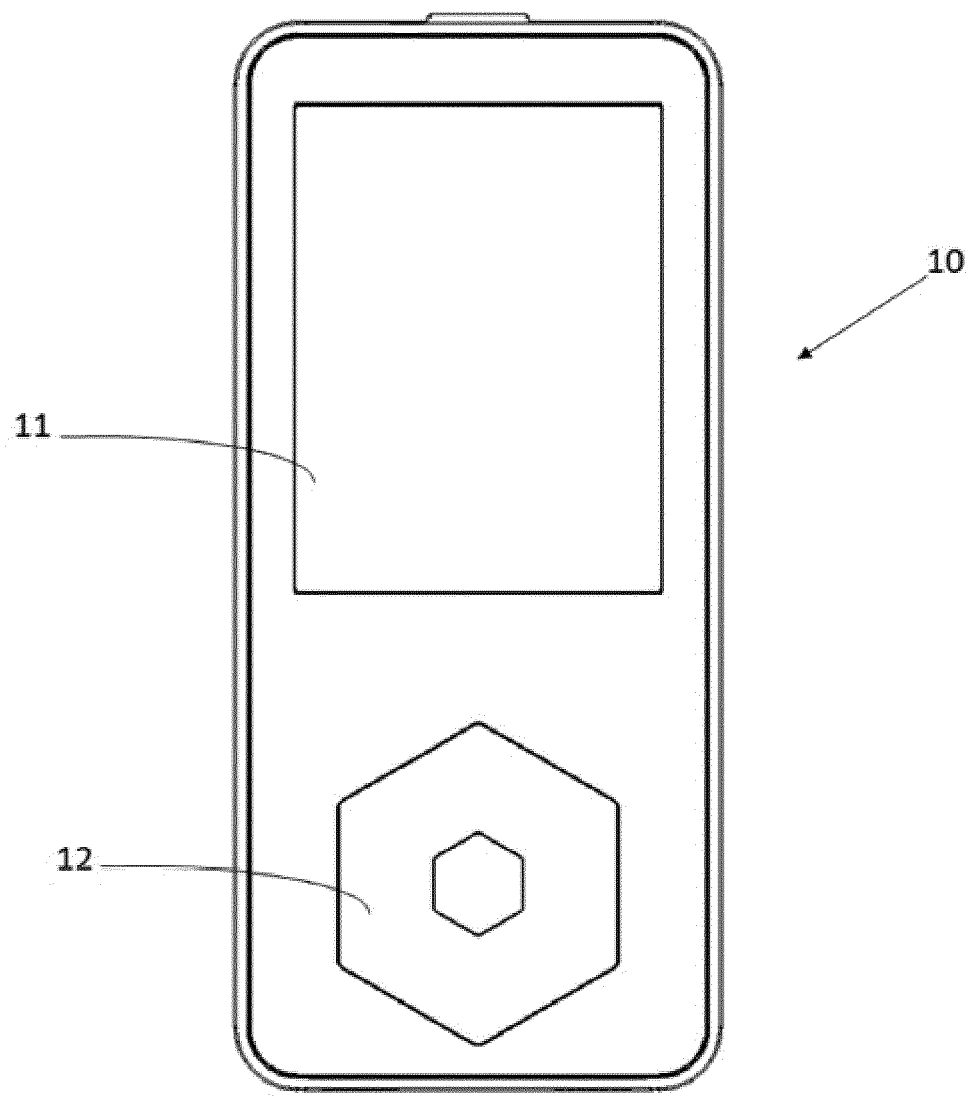
FIG. 2 illustrates a handset of the infusion system for wireless communication with the wearable part.

The control electronics of the pump part 2 includes a transceiver for wireless communication with a user control handset 10 shown in FIG. 2. The handset 10 also includes a transceiver for wireless communication with the pump part 2. The wireless communication may be via Bluetooth™ or other radio frequency near field communication means. The handset 10 includes a graphical user interface 11 and a tactile user interface 12. The handset 10 enables a user to perform the following functions:

Define and store basal profiles;
Transfer an active basal profile to the pump 2;
Define and transmit a bolus request to the pump 2;
Define and transmit a temporary basal to the pump 2;
View a graphical recommendation of a bolus based on glucose readings from a separate blood glucose meter or entered manually following a blood glucose meter reading from a separate blood glucose meter (not shown);
View graphically pump performance over time;
Request the current status of the pump 2 (including what insulin delivery is currently in progress, battery status, alarm conditions, insulin reservoir level, etc).

The handset 10 is also enabled for internet connectivity, e.g. by a wireless radio communication such as Bluetooth™ or Wi-Fi between the handset and remote internet connected devices. The internet connectivity enables two-way patient support either directly or via an intermediate internet connected device such as a PC, laptop or mobile device.

Figure 3:
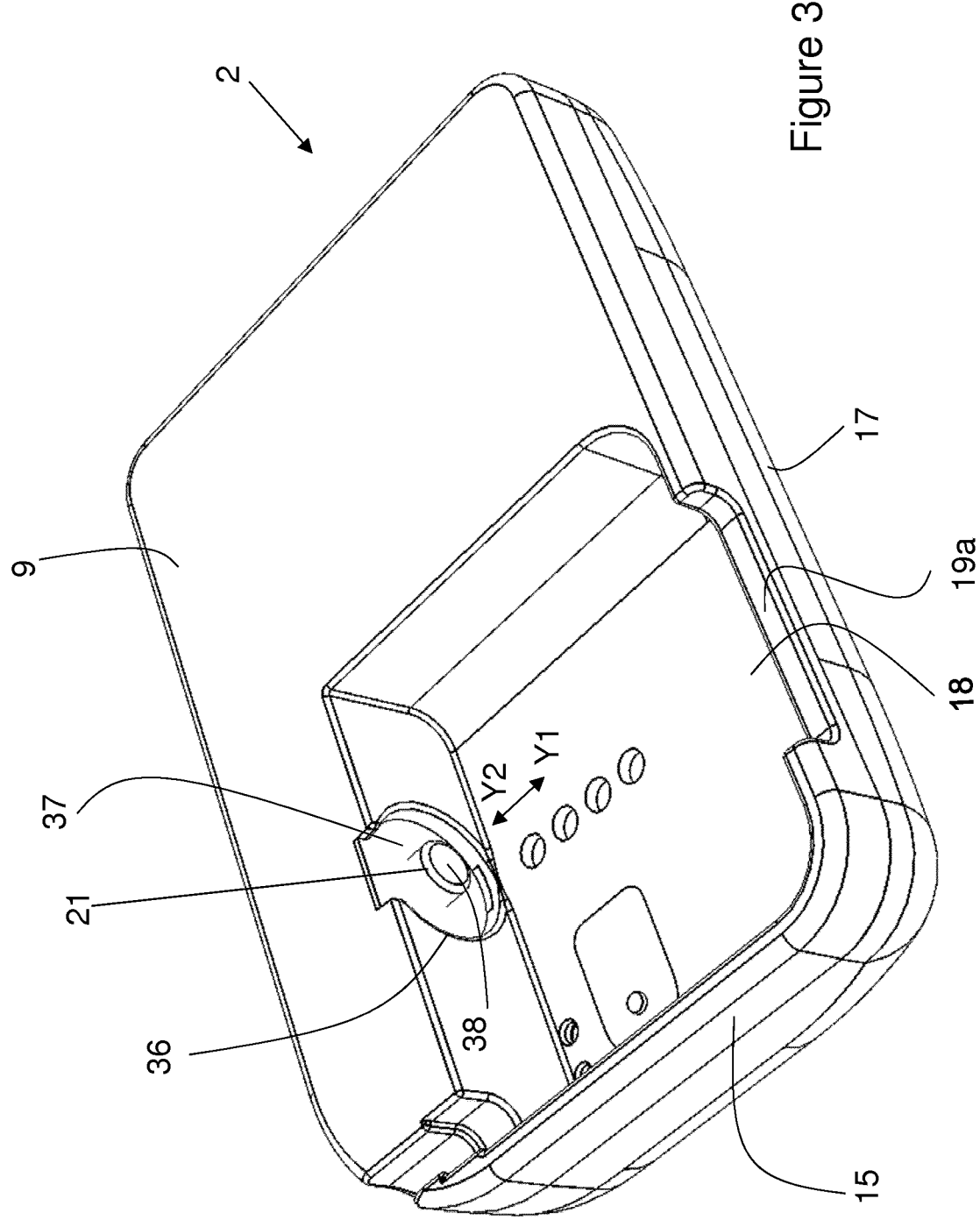
FIG. 3 illustrates a durable pump part of the infusion system.

FIG. 3 shows the pump part 2 with the cartridge 3 removed. The pump part 2 includes an actuator (not visible) arranged to move a drive member 21 in a reciprocating motion. The housing 9 also contains a printed circuit board carrying the control electronics, a piezo-electric sounder, a chassis 15 for supporting the actuator, the PCB, the piezo-electric sounder and defining a battery holder for receiving a rechargeable battery (not shown). The chassis 15 defines a recess 18 for receiving the cartridge 3. The pump part 2 and the cartridge 3 have cooperating retaining features 19a shown in FIGS. 3 and 19b shown in FIG. 1 for the secure retention and ready removal of the cartridge 3 from the pump part 2 using a snap fit type connection.

The drive member 21 is located in an aperture 36 in the housing 9 and is formed as a generally cylindrical piston. The actuator causes the drive member 21 to move in a reciprocating motion in the direction shown by arrow Y1-Y2 in FIG. 3.

The drive member 21 is covered by a membrane 37. The membrane 37 is an elastomeric membrane stretched over a head 38 of the drive member 21. The membrane 37 performs two functions. Firstly, membrane 37 ensures the housing 9 is fluid tight to protect the electrical components therein. Secondly, the membrane 37 provides a biasing function to the drive member 21 to bias the drive member 21 in the direction of arrow Y2. The membrane 37 applies a force in the direction of arrow Y2 throughout the full range of reciprocating motion of the drive member 21. In FIG. 3 the drive member 21 is in its fully extended position having moved in the direction of arrow Y1, so the membrane 37 is stretched to its full extent.

Figure 4:
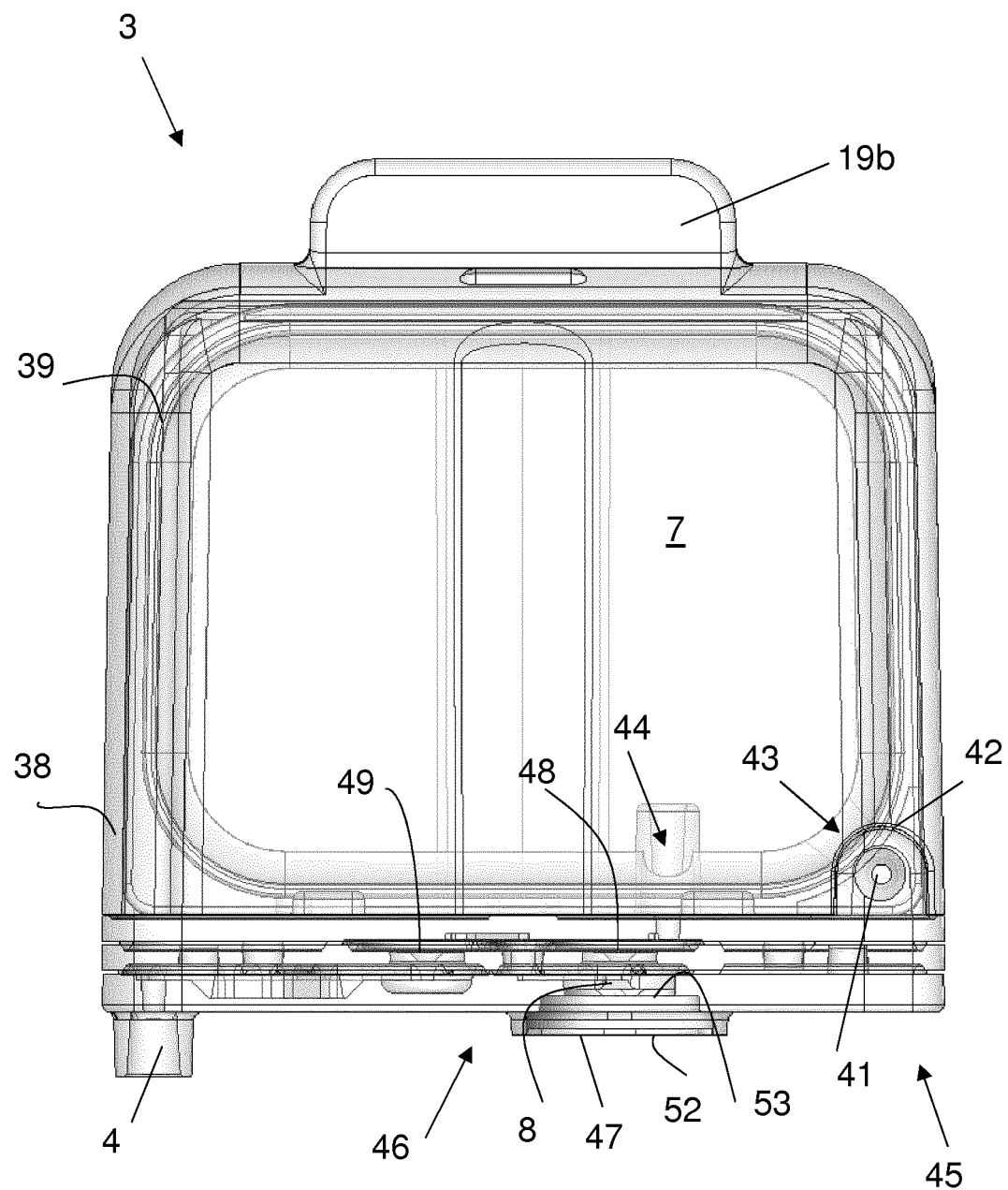
FIG. 4 shows a plan view of the cartridge.
Figure 5:
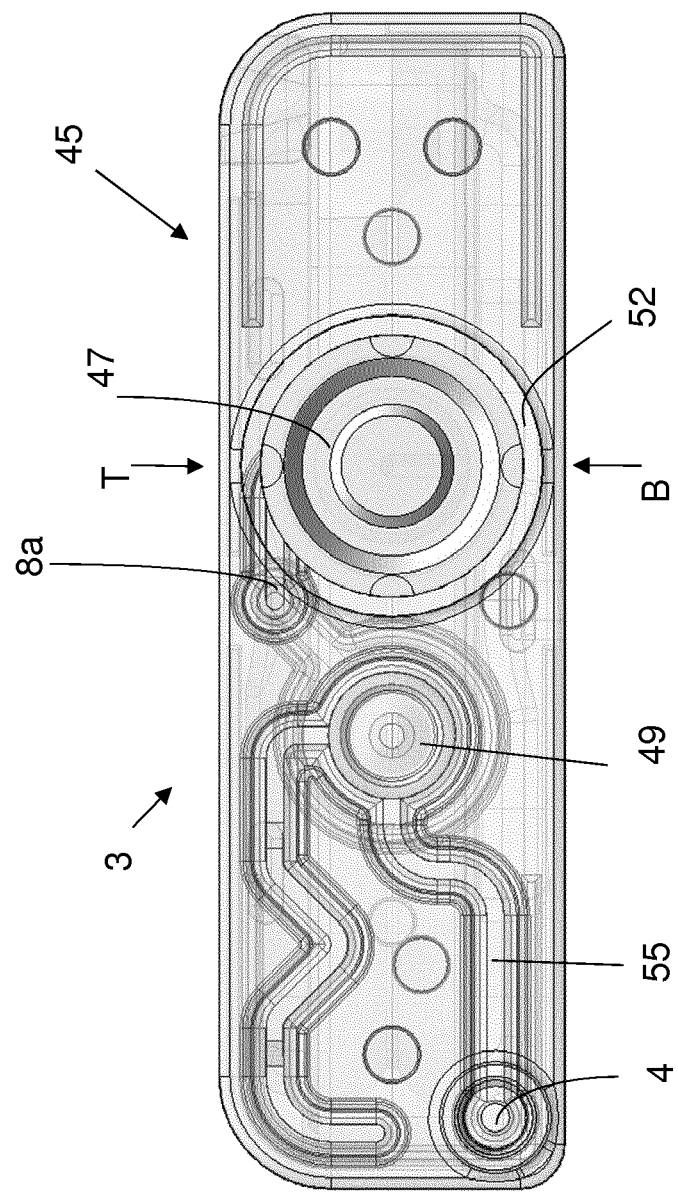
FIG. 5 shows a front view of the cartridge.

The cartridge 3 will now be described in detail with reference to FIGS. 4 and 5. As shown in FIG. 4 the cartridge 3 includes a reservoir case 38 containing the reservoir 7 for storing a supply of insulin. The reservoir 7 is formed as a rectangular frame 39 with front and rear film covers welded onto the frame so as to bound the fluid volume of the reservoir 7. The reservoir 7 fits within the case 38 which provides structural support and protection for the reservoir 7.

At one corner the case 38 includes a filling aperture 41 for receiving a filling needle. Beneath the aperture 41 is a rubberised insert 42 which covers and seals an inlet port 43 of the reservoir 7 passing through the reservoir frame 39. The needle tip penetrates the seal member 42. By connecting a supply of insulin under positive pressure to the filling needle the insulin may be injected through the needle into the inlet port 43 of the reservoir 7 so as to fill the reservoir with insulin. The reservoir frame 39 also includes an outlet port 44 in fluid communication with a pump stack indicated generally by reference number 45.

Figure 6:
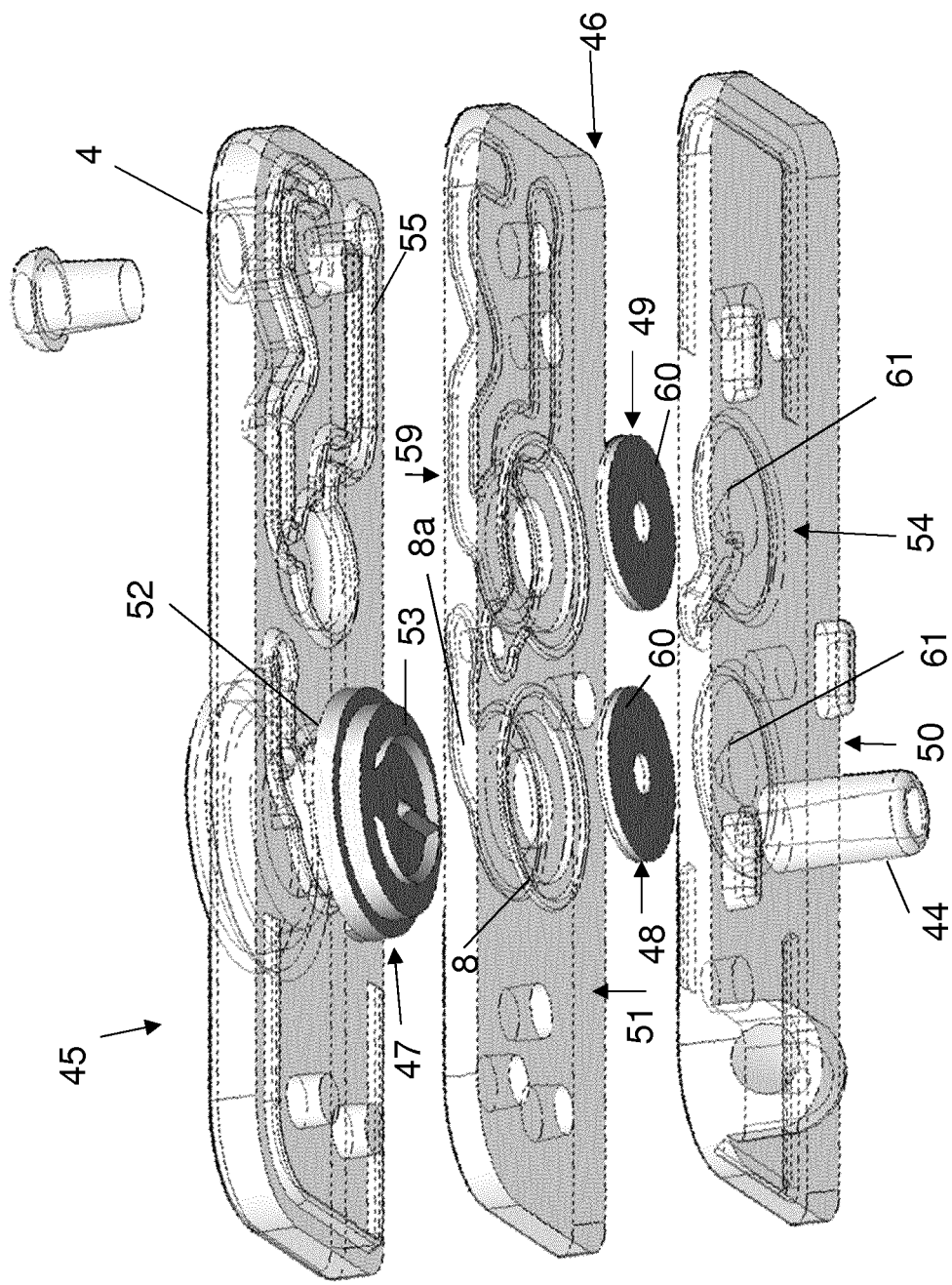
FIG. 6 is a perspective exploded view of part of the cartridge showing the pumping chamber, valves and flow path.

The pump stack 45 includes a valve assembly 46, the pumping chamber 8 having a pumping chamber membrane 47 and the outlet port 4. FIG. 5 illustrates a front view of the cartridge 3 in detail showing the front face of the pump stack 45, and FIG. 6 is an exploded view of the pump stack 45, illustrating the valve assembly 46 in more detail. The valve assembly 46 includes an inlet valve 48 and an outlet valve 49. The inlet valve 48 has an inlet side 50 fluidically connected via the reservoir outlet port 44 to the reservoir 7. The inlet valve 48 also has an outlet side 51 which opens into the pumping chamber 8.

The pumping chamber membrane 47 has a front face 52 and a rear face 53, where the rear face 53 forms a boundary to the pumping chamber 8 such that the displacement of the membrane 47 changes a volume of the pumping chamber 8. The pumping chamber membrane 47 sits adjacent the outlet side 51 of the inlet valve 48. The pumping chamber 8 is bounded by the rear face 53 of the pumping chamber membrane 47 on one side, a front face of the inlet valve member 60 opposing the pumping chamber membrane 47 on a second side and has an internal circumferential wall extending substantially perpendicularly between the inlet valve member 60 and the pumping chamber membrane 47.

The pumping chamber 8 also comprises a fluid passage 8a extending between the outlet side 51 of the inlet valve 48 and an inlet side 59 of the outlet valve 49. The outlet valve 49 also has an outlet side 54 fluidly connected via conduit 55 to the outlet port 4.

The inlet valve 48 and the outlet valve 49 are each one-way check valves and include an annular elastomeric valve member 60 over a conical valve seat 61 such that the conical valve seat 61 projects through the hole in the centre of the annular valve member 60. The outer periphery of the valve member 60 is fixed—by bonding or clamping, for example—within the pump stack 45. The conical valve seat 61 is projected through the hole in the valve member 60 so that the inner periphery of the elastomeric valve member is deflected by the valve seat 61 and the valve seat 61 forms a seal around the inner periphery of the annular valve member. More particularly, the conical valve seat 61 seals onto an edge of the inner periphery of the hole in the annular valve member 60.

The sealing is sufficient to prevent flow of fluid from the inlet side to the outlet side of the respective valve unless the pressure on the inlet side is higher that the pressure on the outlet side and the difference exceeds the breakthough pressure of the valve by providing sufficient force to partially and temporarily lift the valve membrane 60 away from the valve seat 61. The force required to lift the valve member 60 away from the valve seat 61 is the extent to which the valve member 60 is deflected by the valve seat 61, the stiffness of the elastomeric valve seat 60 and the surface finish on the valve seat 61.

During filling of the reservoir 7 and priming of the pumping chamber 8, a filling needle is inserted into filling aperture 41 (shown in FIG. 4). The outlet port 44 provides communication for fluid from the reservoir 7 to the inlet side of the inlet valve 48. When the reservoir 7 is filled with fluid via the filling aperture 41, fluid pressure builds on the inlet side of the inlet valve 48 until it is sufficient to open the inlet valve allowing fluid to enter the pumping chamber 8 thereby priming the pumping chamber ready for pumping. The outlet side of the inlet valve 48 forms the inlet, in this embodiment, to the pumping chamber 8.

Figure 7A:
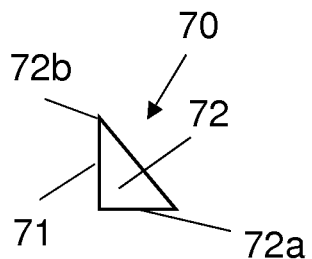
FIG. 7A is a cross section through the rib portion of FIG. 7 at A-A.
Figure 7B:
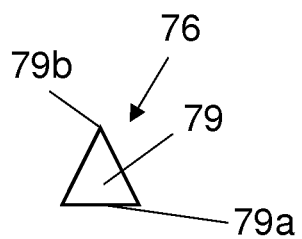
FIG. 7B is a cross section through the rib portion of FIG. 7 at B-B.
Figure 7:
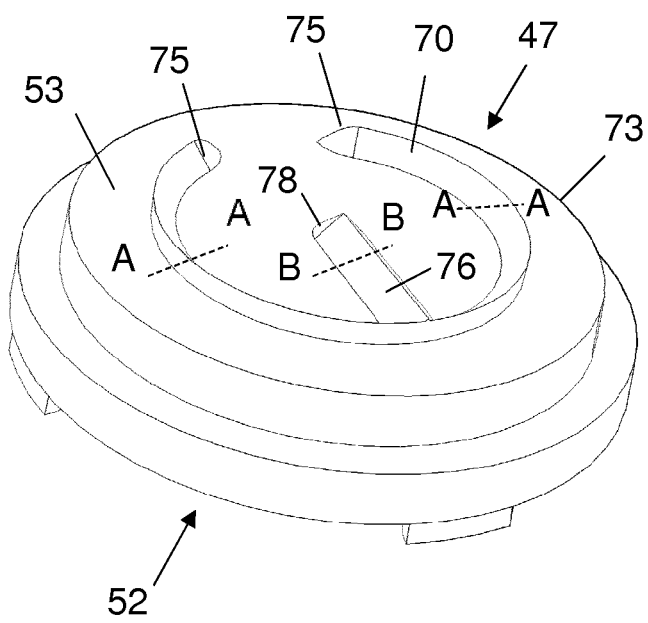
FIG. 7 is a perspective view of an a membrane portion of the pumping chamber having an inwardly projecting rib.

FIG. 7 shows a perspective view of the pumping chamber membrane 47. The front 52 and rear 53 faces of the membrane 47 are generally circular and shaped such that the front face 52 of the membrane 47 cooperates with the aperture 36 in the housing 9, and is acted upon by the drive member 21 in use. The rear face 53 forms part of an interior wall of the pumping chamber 8. The rear face 53 has a first rib portion 70 which projects inwardly in to the bounded volume of the pumping chamber 8. When viewed generally perpendicular to the rear face 53 of the pumping chamber membrane 47, the first rib portion 70 describes an open loop or horseshoe shape on the rear face 53. The first rib portion 70 is generally circular but open, i.e. incomplete, towards the an upper side (when the cartridge in placed on a flat surface with the filling port 41 uppermost) of the rear face 53, in order that the fluid outflow can reach the pumping chamber outlet 8a. Ends 75 of the first rib portion 70 are disposed adjacent the pumping chamber outlet 8a and have tapering profile towards the rear face 53.

In cross section, shown in FIG. 7A, the first rib portion 70 takes the shape of a wedge 72, having a base 72a adjoining the rear face 53 of the membrane 47 and extending to an apex 72b projecting into the pumping chamber 8. The wedge shape defines a substantially right angled triangle such that a side 71 of the first rib portion 70 nearest the outer peripheral edge 73 of the rear face 53 is substantially perpendicular to the rear face 53, projecting inwards and abutting part of the internal circumferential wall of the pumping chamber 8.

When assembled to the pumping chamber 8, the wedge 72 of the first rib portion 70 thereby provides an angled, chamfered edge to the rear face 53 of the chamber 8. The wedge 72 substantially removes the right angled corner which would otherwise be formed between the internal circumferential wall and the rear face 53. The chamfered edge acts to guide the fluid entering the pumping chamber 8 away from the corners of the chamber. Any fluid in contact with the wedge 72 is tracked under a combination of gravity, fluid pressure and surface tension towards a second rib portion 76 near the lower side of the pumping chamber 8.

The second rib portion 76 extends from middle of the first rib portion 70 towards the centre of the rear face 53, in a substantially upright direction and in a generally straight line. The second rib portion 76 has an end 78 with a height which tapers towards the rear face 53 in a similar manner to the ends of the first rib portion 70. The end 78 is located adjacent the outlet side of the inlet valve 48, defining the inlet to the chamber 8. In cross section, shown in FIG. 7B, the second rib portion 76 has a triangular profile 79. The triangular profile differs from the profile of the first rib portion 70 in that the profile 79 forms a central apex 79b tapering from a base 79a adjoining the rear surface 53. Fluid enters the chamber 8 through the inlet valve 48. The second rib portion 76 is designed to break surface tension of fluid entering the pumping chamber 8 and direct the fluid towards the lower side of the chamber 8.

In variations of this embodiment, the cross sectional profile of the inwardly projecting rib may be curved or domed or rectangular, rather than wedge shaped. The curvature may be convex or concave. The ends of the rib portions may taper in a straight line or follow a curvature e.g. a part spherical curvature. In all embodiments the rib may be integrally formed or attached to the movable wall portion, i.e. the membrane 47, of the pumping chamber 8.

Figure 8A:
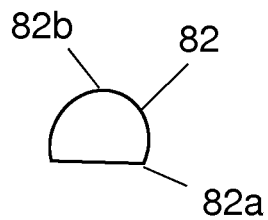
FIG. 8A shows a cross section through the rib portion of FIG. 8 at C-C.
Figure 8:
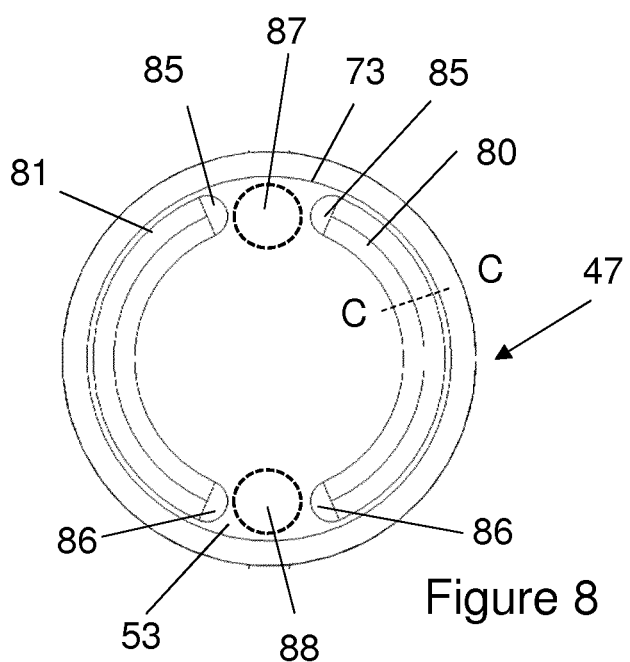
FIG. 8 illustrates a first alternative embodiment of the inwardly projecting rib.

FIGS. 8 to 10 describe alternative arrangements of the inwardly projecting rib which may be used instead of the rib 70 described above. The location of the pumping chamber inlet and outlet may be arranged similarly to that described above, or their location may be altered. In some embodiments there is only a single inlet and a single outlet like in the previously described embodiments, whereas in other embodiments there may be multiple inlets and/or multiple outlets.

FIG. 8 shows two curved ribs 80 and 81 projecting inwardly towards the pumping chamber 8, and located on the rear face 53 of the pumping chamber membrane 47. When viewed perpendicular to the rear face 53, each curved rib 80, 81 is generally concentric with the outer edge 73 of the rear face 53 of the pumping chamber membrane 47. Each curved rib 80, 81 is stepped in a distance from the outer edge 73 and has a first end 85 adjacent an inlet 87 and a second end 86 adjacent an outlet 88. In an alternative embodiment the inlet and outlet locations may be reversed. A gap is formed between the respective ends 85 and a gap is formed between the respective ends 86. The curved ribs 80, 81 are spaced apart, with the first curved rib 80 located to one side of the rear face 53 and the second curved rib 81 located in generally mirror image on the other side of the rear face 53.

In cross section, as shown in FIG. 8A, the ribs 80, 81 have a generally domed shape, providing a curved guiding surface 82 directing the flow away from the outlet 88 towards the inlet 87.

In alternative embodiments, the ribs 80, 81 may have a triangular or curved cross section, and/or vary in length, curvature and/or distance from the centre of the rear face 53. The curvature may be convex or concave. The profile of the first curved rib 80 may vary independently of the second curved rib 81. The ends of the curved ribs 80, 81 may taper in a straight line or follow a curvature e.g. a part spherical curvature.

FIG. 9 shows a single rib 90 projecting inwardly towards the pumping chamber 8, and located on the rear face 53 of the pumping chamber membrane 47. When viewed perpendicular to the rear face 53 of the pumping chamber membrane 47, the single rib 90 is located passing substantially diametrically through the centre of the rear face 53. Each end 95 of the single rib 90 tapers towards the rear face 53. In cross section, as shown in FIG. 9A, the single rib 90 has a generally rectangular shape, guiding the incoming fluid flow and directing the flow away from outlets 96 towards the inlet 97. The plural outlets 96 are located on either side of the rib 90, two nearest the upper side and two nearest the lower side of the pumping chamber 8. The single inlet is substantially centrally located with respect to the membrane 47.

In alternative embodiments, the single rib 90 may have a triangular or curved cross section, vary in length, angle and/or distance from the centre of the rear face 53. The curvature may be convex or concave. The ends of the single rib 90 may taper in a straight line or follow a curvature e.g. part spherical curvature.

FIG. 10 shows a single curved rib 100 projecting inwardly towards the pumping chamber 8, and located on the rear face 53 of the pumping chamber membrane 47. When viewed perpendicular to the rear face 53 of the pumping chamber membrane 47, the single curved rib 100 describes a curved shape on the rear face 53. The curved shape could be described generally as an open loop, and more specifically as an ellipse with one uppermost quadrant removed. The single curved rib 100 has a first end 105 adjacent an inlet 107 to the pumping chamber 8 and a second end 106 adjacent an outlet 108 from the pumping chamber 8. The rib 100 has a first portion 101 curving outwardly from the end 105 towards the edge 73 of the rear face 53 and away from the inlet 107, and a second portion 102 curving outwardly from the end 106 towards the edge 73 of the rear face 53 and meeting the first portion near the lower side of the pumping chamber 8. In this way the rib 100 tracks the fluid entering the pumping chamber via the inlet 107 away from the outlet 108. The curved shape of the rib 100 is configured to generate swirl in the fluid entering the chamber 8, which aids in resisting the formation of occluded air bubbles in the chamber.

In this embodiment, the curvature of the single curved rib 100 does not follow the outer edge 73 of the rear face 53. Instead, the curvature is less than the outer edge 73, and as a result the curved shape is flattened relative to the curvature of the outer edge 73. The second rib portion 102 describes the curvature of the first rib portion 101 in mirror image. In other embodiments, the extent of the curvature of each of the two rib portions 101, 102 as well as the distances from the edge 73 may vary, both symmetrically as well as for each rib portion 101, 102 independently. Each end 105, 106 of the single curved rib 100 has tapers as a smooth curve towards the rear face 53. In alternative embodiments, the ends of the single curved rib 100 may taper in a straight line or follow a curvature e.g. a part spherical curvature.

In cross section, as shown in FIG. 10A, the single curved rib 100 has a generally domed shape, providing a curved guiding surface 103 to the incoming fluid flow and directing the flow away from the outlet 108. The single curved rib 100 has a base 103B adjoining the rear surface 53 rising to a domed peak 103A projecting into the pumping chamber 8. In alternative embodiments the cross sectional shape could be triangular or curved. The curvature may be convex or concave. In addition, the domed peak 103A in this embodiment has a channel recess 104. The channel recess 104 extends along the length of the apex 103b of the single curved rib 100, to assist with breaking surface tension of the fluid. A similar channel recess could be provided in any of the embodiments shown in FIGS. 7 to 9.

The pumping chamber membrane 47 is of an elastomeric material, of a thickness suitable for providing the required flexibility in order to displace a volume of the pumping chamber 8 under the action of the drive member 21 and membrane 37.

During the initial filling of the reservoir 7 with fluid, in this case insulin, the fluid is injected under positive pressure sufficient to exceed the breakthrough pressure of the inlet valve 48, which may be set at approximately 100 millibars. In practice, the breakthrough pressure may be in the range of approximately 10 to approximately 500 millibars. This equates to a relatively low tension in the elastomeric valve member 60 of typically less than 1 Newton.

When the pressure in the reservoir 7 during filling exceeds the breakthrough pressure of the inlet valve 48, fluid flows from the reservoir 7 through the reservoir outlet port 44 and into the pumping chamber 8. Fluid enters the pumping chamber 8 via the open annulus between the valve member 60 and the valve seat 61, located generally in the centre of valve member 60 when viewed perpendicular to the valve member face. The fluid in the pumping chamber 8 then starts to build pressure on the inlet side of the outlet valve 49. When the device is first filled, the pumping chamber 8 contains air, which must be expelled from the device via the infusion set before use. As fluid enters the chamber 8, the inwardly projecting rib portions 70, 76 (or ribs 80, 81, 90, 100) ensure that fluid and fluid droplets do not form and the fluid filling the pumping chamber forms as far as possible as single fluid front. Air in the chamber 8 is forced towards the outlet of the chamber and is progressively compressed by the incoming fluid, building pressure on the inlet side of the outlet valve 49.

Once the positive pressure differential between the inlet side and the outlet side of the outlet valve 49 exceeds the breakthrough pressure of the outlet valve 49 the outlet valve 49 opens and the air followed by the fluid passes via conduit 55 to the outlet port 4 of the cartridge 3. With the infusion tube 6 and infusion set 5 connected to the outlet port 4 of the cartridge 3 the air and then insulin flows to the infusion set 5. The air, as well as air present in the infusion tube 6 and the infusion set 5 is expelled, until the insulin begins to exit the infusion set 5 indicating that the reservoir 7 is full and the infusion set 5 is primed ready for use.

At this point the injection of insulin through the filling needle into the filling aperture 41 can be stopped, and the pressures in the valve apparatus 46 and the reservoir 7 will return to ambient causing the inlet valve 48 and the outlet valve 49 to close leaving a positive pressure in the valve apparatus 46. Removal of the filling needle from the filling aperture 41 causes the seal insert 42 to seal the reservoir 7 to prevent escape of insulin from the filling aperture 41. The filled and primed cartridge 3 having the infusion set 5 connected is now ready for coupling to the pump part 2, in readiness for use in providing ongoing repetitive dosing to the patient.

As explained above the drive member 21 of the actuator rests in a fully extended position in the direction of arrow Y1 in FIG. 3 such that upon installation of the cartridge 3 in the pump part 2 the aperture membrane 37 stretched over the head 38 of the drive member 21 directly contacts the front face 52 of the pumping chamber membrane 47 so as to deflect the pumping chamber membrane 47 inwardly into the pumping chamber 8 thereby decreasing the volume of the pumping chamber 8. Since the pumping chamber 8 is fully filled with insulin (i.e. there are no gas bubbles which may cause a fluid front) the pressure in the pumping chamber temporarily increases at the inlet side 53 of the outlet valve 49 which opens releasing a very small volume of insulin from the outlet valve 49 which exits via the outlet port 4 and from the infusion set 5. This displacement of the pumping chamber 8 is of the order of 10 microlitres or less and preferably is 2.5 microlitres or less.

By successively energising the actuator the drive member 21 is caused to move in reciprocating motion in the directions of arrows Y1 and Y2 in FIG. 3 which, by displacement of the pumping chamber membrane 47, causes successive opening and closing of the inlet valve 48.

When the actuator causes the drive member 21 to retract in the direction of arrow Y2 in FIG. 3, the pumping chamber membrane 47 partially relaxes out from the pumping chamber. The volume of the pumping chamber is thereby increased, decreasing the pressure in the pumping chamber 8. The resulting positive pressure differential between the inlet side 50 and the outlet side 51 of the inlet valve 48 increases above the breakthrough pressure of the inlet valve, so that the inlet valve 48 opens and the pumping chamber 8 fills with insulin from the reservoir 7.

When the actuator causes the drive member 21 to extend in the direction of arrow Y1 it causes stretching the pumping chamber membrane 48 into the pumping chamber. The resulting decrease in volume of the pumping chamber 8 increases the pressure in the pumping chamber 8. The positive pressure differential between the inlet side 53 and the outlet side 54 of the outlet valve 49 thereby increases above the breakthrough pressure of the outlet valve 49. The outlet valve 49 then opens and insulin flows through the outlet valve and via the outlet port 4 to the infusion set 5 for delivery of insulin to the patient.

Using the handset 10 the control electronics in the circuit board 13 of the pump part 2 may be controlled to activate the actuator 20 to provide the required delivery profile of insulin to the patient.

The cartridge 3 may be exchanged for a full cartridge when empty and refilled as described above.

Although the invention has been described above with reference to one or more preferred embodiments, it will be appreciated that various changes or modifications may be made without departing from the scope of the invention as defined in the appended claims.

The invention claimed is:

1. A pumping chamber for a micro-pump, the pumping chamber having a volume of 100 microlitres or less bounded by an interior wall and having an inlet and an outlet, wherein a portion of the interior wall is movable so as to vary the pumping chamber volume and the interior wall has at least one inwardly projecting rib having a first end adjacent the inlet and a second end adjacent the outlet.

2. The pumping chamber according to claim 1, wherein the inwardly projecting rib has a generally wedge shaped cross section.

3. The pumping chamber according to claim 2, wherein the inwardly projecting rib section has a base connected to the interior wall and tapers to an apex opposite the base of the rib.

4. The pumping chamber according to claim 2, wherein the inwardly projecting rib section has a base connected to the interior wall, and an edge projecting generally perpendicular to the base of the rib.

5. The pumping chamber according to claim 1, wherein the inwardly projecting rib has a generally dome shaped cross section.

6. The pumping chamber according to claim 5, wherein the inwardly projecting rib section has a base connected to the interior wall, and a domed peak opposite the base.

7. The pumping chamber according to claim 6, wherein the domed peak includes a channel recess.

8. The pumping chamber according to claim 1, wherein the inwardly projecting rib has a rectangular shaped cross section.

9. The pumping chamber according to claim 1, wherein the inwardly projecting rib has a height and a length, and the rib height reduces in the length direction towards at least one of the first and second ends of the rib.

10. The pumping chamber according to claim 1, wherein the at least one inwardly projecting rib is formed as a plurality of ribs, or as a plurality of rib portions.

11. The pumping chamber according to claim 10, wherein the plurality of ribs or rib portions intersect.

12. The pumping chamber according to claim 1, wherein the inwardly projecting rib includes a substantially straight portion.

13. The pumping chamber according to claim 1, wherein the inwardly projecting rib includes a curved portion.

14. The pumping chamber according to claim 13, wherein the at least one inwardly projecting rib having a curved portion forms an open or incomplete loop.

15. The pumping chamber according to claim 1, wherein the inwardly projecting rib is connected to and movable with the movable portion of the interior wall.

16. The pumping chamber according to claim 1, wherein the movable portion of the wall is formed of elastomeric material.

17. The pumping chamber according to claim 1, wherein the pumping chamber is configured such that fluid flow through the inlet is substantially perpendicular to a portion of the interior wall having the inwardly projecting rib.

18. The pumping chamber according to claim 1, wherein the inlet is located on an opposite side of the interior wall to the outlet.

19. An infusion system for the infusion of a liquid therapeutic product, the system comprising:
   a reservoir for storing the liquid therapeutic product; and
   a pump having a pumping chamber, the pumping chamber having a volume of 100 microlitres or less bounded by an interior wall and having an inlet and an outlet, wherein a portion of the interior wall is movable so as to vary the pumping chamber volume and the interior wall has at least one inwardly projecting rib having a first end adjacent the inlet and a second end adjacent the outlet.

20. The pumping chamber according to claim 1, wherein the rib is arranged for guiding fluid from adjacent the outlet towards the inlet during priming of the pumping chamber.

\* \* \* \* \*